(12) United States Patent
Chia et al.

(10) Patent No.: US 11,175,462 B2
(45) Date of Patent: Nov. 16, 2021

(54) SPLIT SURGICAL LASER FIBER

(75) Inventors: Wen-Jui Ray Chia, Sunnyvale, CA (US); Steven Yihlih Peng, Fremont, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 616 days.

(21) Appl. No.: 14/237,633

(22) PCT Filed: Sep. 6, 2012

(86) PCT No.: PCT/US2012/053849
§ 371 (c)(1),
(2), (4) Date: Feb. 7, 2014

(87) PCT Pub. No.: WO2013/036566
PCT Pub. Date: Mar. 14, 2013

(65) Prior Publication Data
US 2014/0188096 A1    Jul. 3, 2014

Related U.S. Application Data

(60) Provisional application No. 61/532,819, filed on Sep. 9, 2011, provisional application No. 61/614,143, filed on Mar. 22, 2012.

(51) Int. Cl.
*G02B 6/38*     (2006.01)
*A61B 90/98*    (2016.01)
(Continued)

(52) U.S. Cl.
CPC ............ *G02B 6/3813* (2013.01); *A61B 90/98* (2016.02); *G02B 6/00* (2013.01); *G02B 6/3812* (2013.01);
(Continued)

(58) Field of Classification Search
CPC .......... A61B 90/98; A61B 2017/00473; A61B 2017/00482; A61B 2018/00178;
(Continued)

(56) References Cited

U.S. PATENT DOCUMENTS 3,247,506 A * 4/1966 Grim, Jr. ................. H03M 1/00
341/14
3,834,391 A * 9/1974 Block .................. A61B 18/203
606/9

(Continued)

FOREIGN PATENT DOCUMENTS

GB        2020056 A  * 11/1979   .......... G02B 6/3869
WO    2006031632 A2     3/2006
WO    2013036566 A1     3/2013

OTHER PUBLICATIONS

Single, Multi & Hybrid Fibre Optic Connectors, LEMO SA, Switzerland, Apr. 2002.*
(Continued)

*Primary Examiner* — Carl H Layno
*Assistant Examiner* — Michael J Lau
(74) *Attorney, Agent, or Firm* — Bookoff McAndrews, PLLC (57) ABSTRACT

A surgical laser tool comprises an output member that includes an output laser fiber, a probe tip, and electrical contacts. The probe tip is attached to a distal end of the output laser fiber. Electromagnetic energy transmitted through the output laser fiber is discharged through the probe tip. The electrical contacts are supported at a proximal end of the output member.

20 Claims, 6 Drawing Sheets

(51) Int. Cl.
  *G02B 6/00* (2006.01)
  *A61B 18/00* (2006.01)
  *A61B 17/00* (2006.01)

(52) U.S. Cl.
  CPC .. *G02B 6/3825* (2013.01); *A61B 2017/00473* (2013.01); *A61B 2017/00482* (2013.01); *A61B 2018/00178* (2013.01); *A61B 2018/00642* (2013.01); *A61B 2018/00988* (2013.01); *G02B 6/3807* (2013.01)

(58) Field of Classification Search
  CPC .......... A61B 2018/00642; A61B 2018/00988; G02B 6/00; G02B 6/3813; G02B 6/3825; G02B 6/3807
  USPC .......................................................... 606/16
  See application file for complete search history.

(56) References Cited

U.S. PATENT DOCUMENTS

| | | | | |
|---|---|---|---|---|
| 4,828,353 A * | 5/1989 | Yamaguchi | ............... | G02B 6/32 385/58 |
| 4,964,685 A * | 10/1990 | Savitsky | ............... | G02B 6/3855 385/58 |
| 5,058,983 A * | 10/1991 | Corke | ................... | G02B 6/243 385/78 |
| 5,085,492 A * | 2/1992 | Kelsoe | ................. | G02B 6/3813 385/60 |
| 5,166,995 A * | 11/1992 | Briggs | ................. | G02B 6/3807 385/58 |
| 6,009,339 A * | 12/1999 | Bentsen | ................. | G01N 21/05 600/322 |
| 6,305,849 B1 * | 10/2001 | Roehrs | .................... | B41J 2/175 385/59 |
| 6,367,986 B1 * | 4/2002 | Inagaki | ..................... | C08J 3/24 385/134 |
| 6,848,834 B1 * | 2/2005 | Roehrs | ................... | G02B 6/383 385/59 |
| 7,909,817 B2 | 3/2011 | Griffin et al. | | |
| 9,055,987 B2 * | 6/2015 | Hulliger | ............. | A61B 17/8863 |
| 2002/0012502 A1 | 1/2002 | Farrar et al. | | |
| 2003/0059171 A1 * | 3/2003 | Pfleger | ................ | G02B 6/3895 385/75 |
| 2004/0122419 A1 * | 6/2004 | Neuberger | ............ | A61B 18/22 606/10 |
| 2004/0266257 A1 * | 12/2004 | Ries | ..................... | G02B 6/4298 439/577 |
| 2006/0251360 A1 * | 11/2006 | Lu | ............................ | G02B 6/43 385/88 |
| 2008/0045921 A1 * | 2/2008 | Anderson | ......... | A61M 25/0102 604/508 |
| 2009/0048588 A1 | 2/2009 | Peng et al. | | |
| 2009/0131922 A1 * | 5/2009 | Dewey | ................ | A61B 18/203 606/9 |
| 2009/0259220 A1 * | 10/2009 | Appling | ................ | A61B 18/20 606/10 |
| 2010/0074616 A1 * | 3/2010 | Kewitsch | ............ | G02B 6/4202 398/38 |
| 2010/0284655 A1 * | 11/2010 | Nakano | .................. | G02B 6/387 385/78 |
| 2010/0329612 A1 * | 12/2010 | Everett | ................ | G02B 6/3807 385/74 |
| 2011/0008006 A1 * | 1/2011 | Weinrotter | ........... | G02B 6/3849 385/92 |
| 2011/0091166 A1 * | 4/2011 | Benjamin | .......... | G02B 6/02033 385/81 |
| 2011/0103749 A1 * | 5/2011 | Hogue | ................ | G02B 6/3871 385/81 |
| 2011/0293223 A1 * | 12/2011 | Shimazu | ................ | H01R 4/18 385/81 |
| 2012/0157977 A1 * | 6/2012 | Hulliger | ............... | A61B 17/866 606/13 |
| 2013/0011102 A1 * | 1/2013 | Rinzler | ................ | G02B 6/3813 385/89 |

OTHER PUBLICATIONS

EPO Communication from European Patent Application No. 12766503.2, dated May 27, 2014.
International Search Report and Written Opinion of PCT/US2012/053849, dated Dec. 19, 2012.
Examination Report dated Dec. 5, 2016, in corresponding European Patent Application No. 12766503.2-1666 (5 pages).

* cited by examiner

FIG. 9

SPLIT SURGICAL LASER FIBER

CROSS-REFERENCE TO RELATED APPLICATION

This Application is a Section 371 National Stage Application of International Application No. PCT/US2012/053849, filed Sep. 6, 2012 and published as WO 2013/036566 A1 on Mar. 14, 2013, in English, and claims the benefit of U.S. Provisional Application Ser. No. 61/532,819, filed Sep. 9, 2011 and U.S. Provisional Application Ser. No. 61/614,143, filed Mar. 22, 2012. Each of the above-referenced applications are hereby incorporated by reference in their entirety.

BACKGROUND

Embodiments of the present invention generally relate to surgical laser systems and, more specifically, to a split laser fiber and a surgical tool that includes the split laser fiber.

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol. Surgical laser systems typically generate the laser energy in a laser resonator. The laser energy is delivered to a targeted treatment site through an optical fiber.

Different laser surgical treatments often require different types of optical fibers. For instance, a side-firing optical fiber delivers or discharges the laser energy in a lateral direction relative to the longitudinal axis of the fiber. This type of fiber is typically used in cavity wall ablation treatments, such as those used to treat benign prostatic hyperplasia (BPH), for example. An end-firing optical fiber discharges the laser energy along the longitudinal axis of the fiber. Exemplary uses of the end-firing optical fiber include ablating tumors and disintegrating kidney or bladder stones or renal stones.

SUMMARY

Embodiments of the invention are directed to a surgical laser tool that may be used to perform a surgical laser treatment on a patient. In one embodiment, the surgical laser tool comprises an output member that includes an output laser fiber, a probe tip, and electrical contacts. The probe tip is attached to a distal end of the output laser fiber. Electromagnetic energy transmitted through the output laser fiber is discharged through the probe tip. The electrical contacts are supported at a proximal end of the output member.

In one embodiment, the tool comprises an extension member having an extension laser fiber. The extension member has a distal end that is removably coupled to the proximal end of the output member. An optical coupler optically connects a distal end of the extension laser fiber to a proximal end of the output laser fiber. In one embodiment, the extension member comprises electrical contacts that are configured to engage electrical contacts of the output member when the extension member is coupled to the output member.

Another embodiment is directed to a method. In one embodiment of the method, a proximal end of an output member is attached to a distal end of an extension member. Electromagnetic energy from a laser source is delivered through an extension laser fiber of the extension member and an output laser fiber of the output member. The electromagnetic energy is discharged from a probe tip attached to a distal end of the output laser fiber.

DETAILED DESCRIPTION OF ILLUSTRATIVE EMBODIMENTS

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 1:
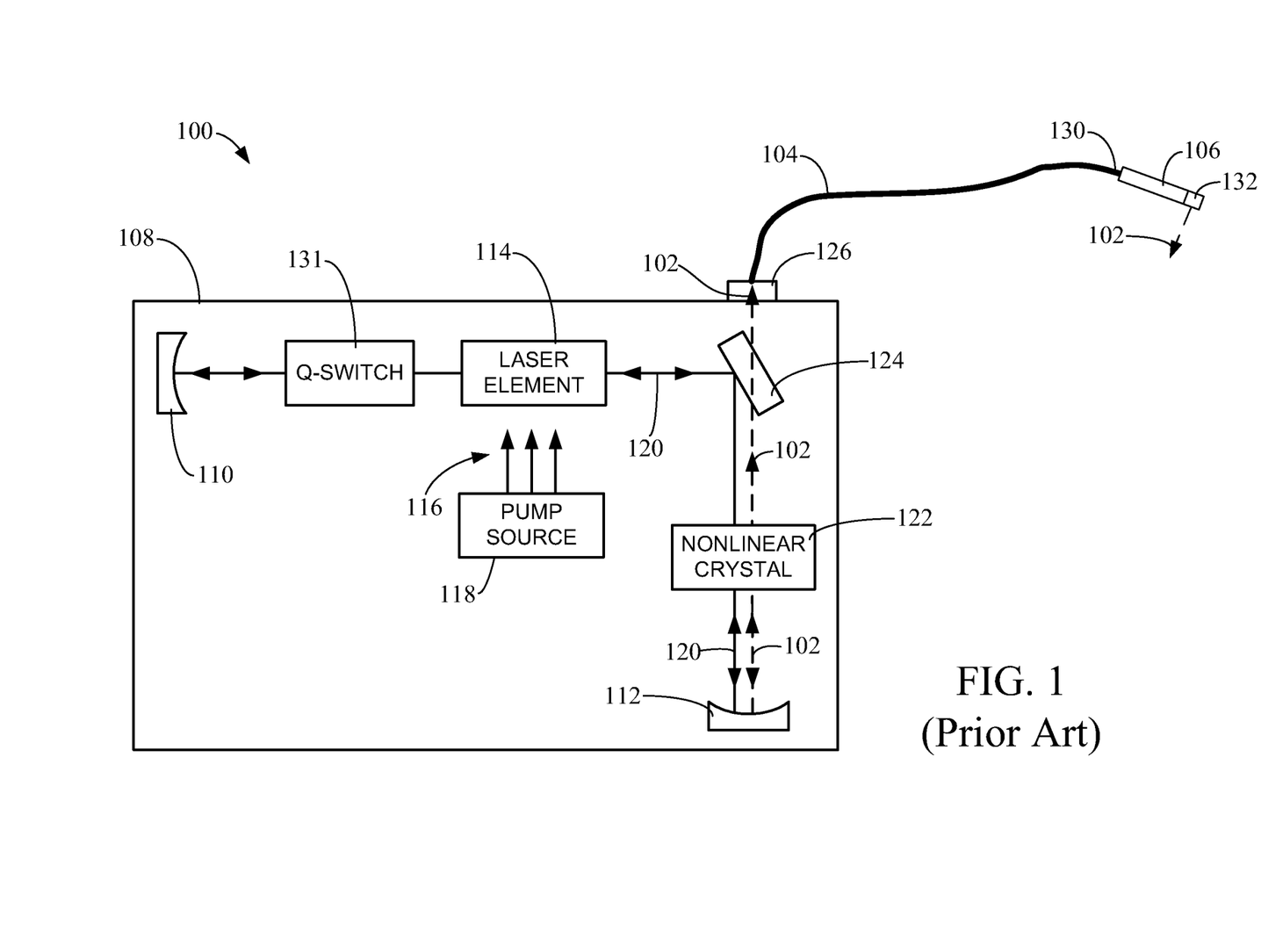
FIG. 1 is a simplified diagram of an exemplary surgical laser system in accordance with the prior art.

FIG. 1 is a simplified diagram of an exemplary surgical laser tool or system 100 in accordance with the prior art. In general, the laser system 100 is configured to generate electromagnetic radiation 102 in the form of a laser beam, deliver the electromagnetic radiation through a laser fiber 104, such as a waveguide or optical fiber, to a probe tip 106 where it is discharged to a desired target, such as tissue of a patient.

The exemplary system 100 comprises a laser source 108, such as the exemplary laser resonator illustrated in FIG. 1. The laser resonator 108 may include a first resonator mirror 110, a second resonator mirror 112 and a laser rod or element 114. In one embodiment, the laser element 114 comprises a yttrium-aluminum-garnet crystal rod with neodymium atoms dispersed in the YAG rod to form a Nd:YAG laser element. Other conventional laser elements 114 may also be used.

The laser element 114 is pumped by a light input 116 from an optical pump source 118, such as a Kr arc lamp or other conventional pump source such as diode laser, to produce laser light or beam 120 at a first frequency. The laser resonator 108 also includes a nonlinear crystal 122, such as a lithium borate (LBO) crystal or a potassium titanyl phosphate crystal (KTP), for generating a second harmonic of the laser beam 120 emitted by the laser element 114. The laser beam 120 inside the resonator 108 bounces back and forth between the first and second resonator mirrors 110 and 112, reflects off a folding mirror 124 and propagates through the laser element 114 and nonlinear crystal 122. The laser element 114 has optical gain at a certain wavelength and this determines the wavelength of the laser beam 120 inside the resonator 108. This wavelength is also referred to as the fundamental wavelength. For the Nd:YAG laser element 114, the fundamental wavelength is 1064 nm.

A Q-switch 131 may be used in the resonator 108 to convert the laser beam 120 to a train of short pulses with high peak power. These short pulses increase the conversion efficiency of the second harmonic laser beam 102 and increase the average power of the laser beam 102 outside the resonator 108.

When the laser beam 120 inside the resonator 108 propagates through the nonlinear crystal 122 in a direction away from the folding mirror 124 and toward the second resonator mirror 112, a beam 102 of electromagnetic radiation at the second harmonic wavelength is output from the crystal 122. The second resonator mirror 112 is highly reflective at both the fundamental and second harmonic wavelengths, and both beams 120 and 102 propagate back through the nonlinear crystal 122. On this second pass, more beams 102 at the second harmonic wavelength are produced. For example, the nonlinear crystal 122 can produce a laser beam 102 having a wavelength of approximately 532 nm (green) when a Nd:YAG rod is used as the laser element 114. One advantage of the 532 nm wavelength is that it is strongly absorbed by hemoglobin in blood and, therefore, is useful for cutting, vaporizing and coagulating vascular tissue.

The folding minor 124 is highly reflective at the fundamental wavelength and is highly transmissive at the second harmonic wavelength. Thus, the laser beam 102 at the second harmonic passes through the folding minor 124 and produces a second harmonic laser beam 102 outside the optical resonator 108. The laser fiber 104 connects to an optical coupler 126, which couples the beam 102 to the laser fiber 104 through a shutter mechanism (not shown). The beam 102 travels through the laser fiber 104 to the probe 106 coupled to a distal end 130 of the laser fiber 104. Embodiments of the probe 106 include components that support the distal end 130 of the laser fiber, such as an endoscope or cystoscope.

The probe 106 generally includes a probe tip 132 where the laser beam 102 is discharged. The probe tip 132 may include a fiber cap that is attached to the distal end of the optical fiber 104. The laser energy may be directed laterally from the probe tip by reflecting the laser energy off a polished beveled surface at the distal end of the laser fiber 104. The fiber cap generally seals a cavity containing a gas (or vacuum) that maintains the necessary refractive index difference for total internal reflection at the beveled surface. Alternatively, the probe tip 132 may be an end-fire probe tip configured to discharge the laser beam 102 along the axis of the fiber 104. Other types of probe tips 132 may also be used.

The laser system 100 may be controlled by a surgeon through a suitable interface. The controls include a controller for selectively opening the shutter of the system 100 to allow for continuous or pulsed discharge of the laser beam 102 through the probe 106. The laser fiber 104, the probe 106 and the probe tip 132 are replaced after each laser surgery.

Figure 2:
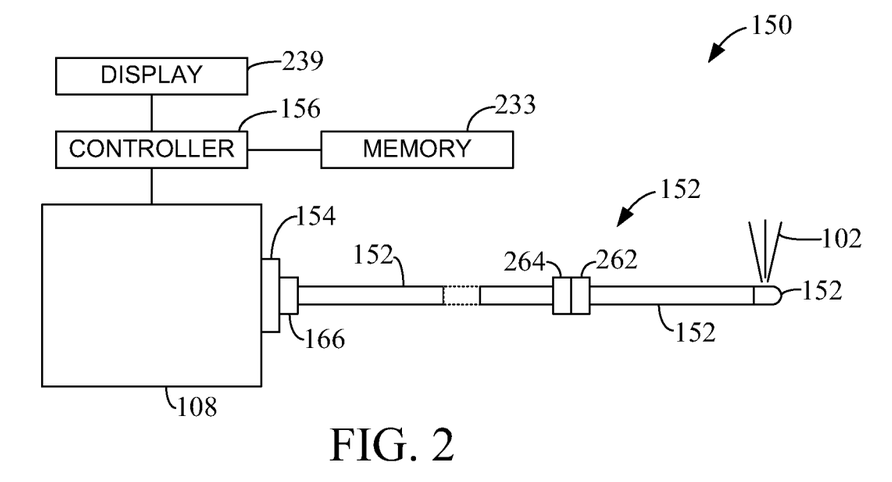
FIG. 2 is a simplified diagram of a surgical laser tool or system formed in accordance with embodiments of the invention.
Figure 3:
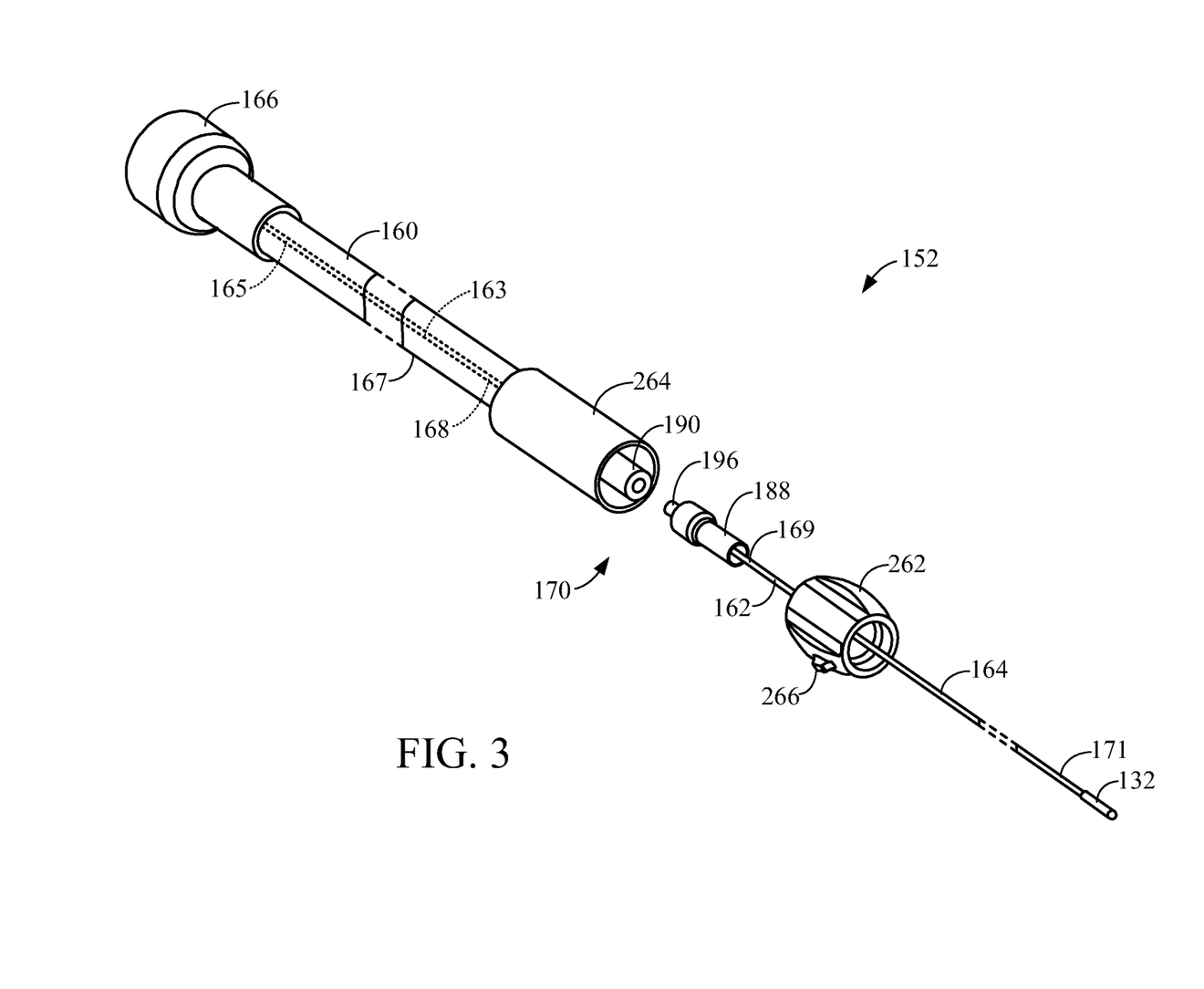
FIG. 3 is an exploded isometric view of a split laser fiber 152 in accordance with embodiments of the invention.

FIG. 2 is a simplified diagram of a surgical laser tool or system 150 that includes a split laser fiber 152 formed in accordance with embodiments of the invention. FIG. 3 is an exploded isometric view of a split laser fiber 152 in accordance with embodiments of the invention.

In some embodiments, the laser system or tool 150 may include conventional components such as a conventional laser source 108 and a shutter mechanism 154 for generating and discharging a laser beam 102 to the laser fiber 152. Additionally, the system 150 may include a controller 156 that may be used by an operator of the system 150 to adjust settings, control the shutter mechanism 154, and perform other functions.

In one embodiment, the split laser fiber 152 includes an extension member 160 and an output member 162, which are removably coupled together. The extension member 160 and the output member 162 respectively include an extension laser fiber 163 and an output laser fiber 164, shown in FIG. 3, which are conventional optical fiber waveguides used to transmit electromagnetic energy, such as the laser beam 102. The extension laser fiber 163 includes a proximal end 165 that is coupled to the laser beam discharged through the shutter mechanism 154 using a suitable optical coupler 166. In one embodiment, the extension member 160 includes a sleeve or tube 167 (FIG. 3) that may enclose the extension laser fiber 163, wires, and other components extending from the laser source 108 toward the distal end 168.

In one embodiment, the extension member 160 is much longer than the output member 162 and operates to deliver the electromagnetic energy or laser beam 102 over the extension laser fiber 163 the greatest distance along the split laser fiber 152. This results in a reduction of waste relative to conventional systems that utilize a single laser fiber. Rather than discarding the entire laser fiber, as is typically necessary in the single fiber systems, only the short output member 162 must be discarded after use. The extension member 160 may be re-used many times with different output members 162.

The extension laser fiber 163 includes a distal end 168 that is optically coupled to a proximal end 169 of the output laser fiber using a suitable optical coupler 170. This optical coupling couples the electromagnetic energy 102 delivered through the extension laser fiber 163 to the output laser fiber 164 for further transmission through the output laser fiber 164 to a conventional probe tip 132 (e.g., side-fire probe tip, end-fire probe tip, etc.) located at the distal end 171, as shown in FIGS. 2 and 3.

Figure 4:
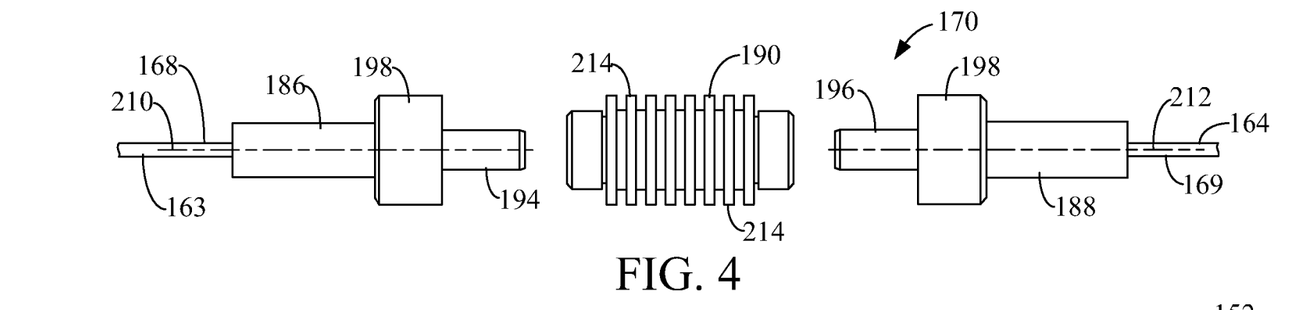
FIG. 4 is an exploded side view of an exemplary optical coupler in accordance with embodiments of the invention.
Figure 5:
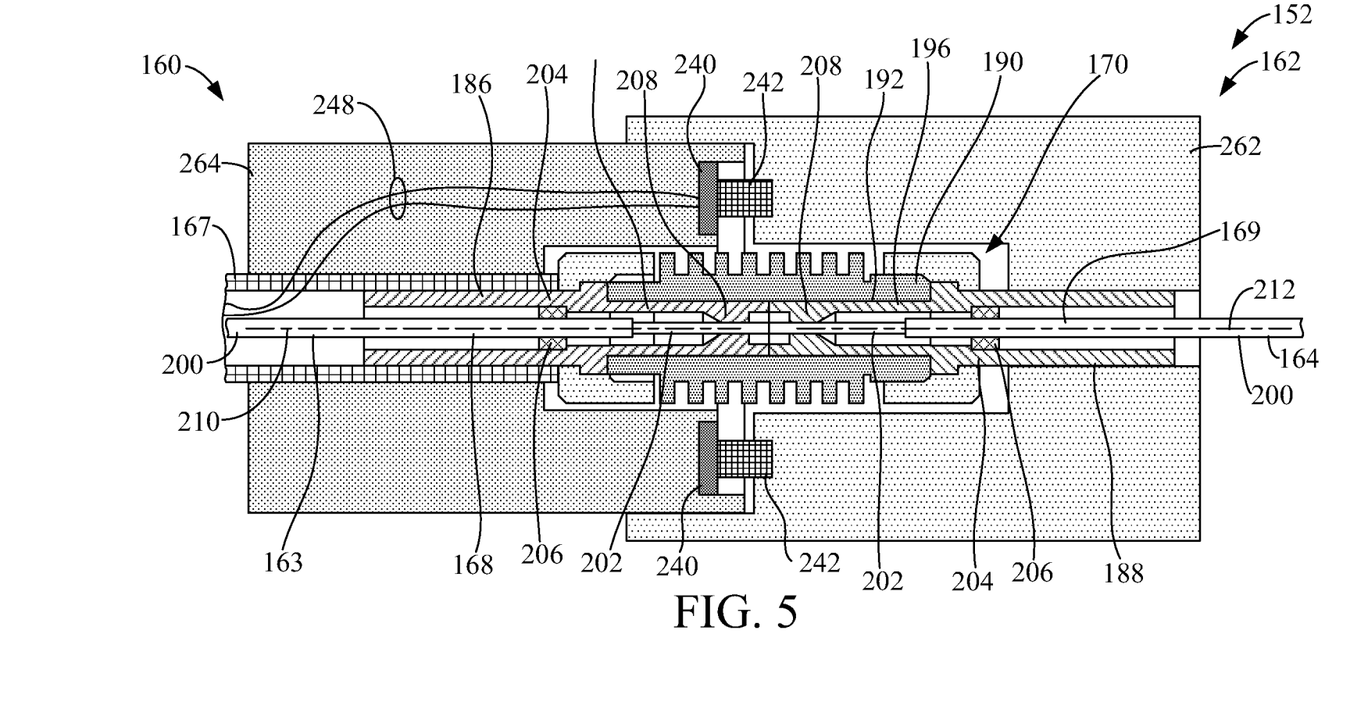
FIG. 5 is a side cross-sectional assembled view of the optical coupler of FIG. 4 and additional components of the split laser fiber in accordance with embodiments of the invention.

The optical coupler 170 can take on many forms while providing the desired optical coupling function. In one embodiment, the optical coupler 170 aligns the distal end 168 of the extension laser fiber 163 with the proximal end 169 of the output laser fiber 164 to allow for electromagnetic energy 102 transmitted through the extension laser fiber 163 to be coupled to the output laser fiber 164 for further transmission to the probe tip 132. FIG. 4 is an exploded side view of an exemplary optical coupler 170 in accordance with embodiments of the invention. FIG. 5 is a side cross-sectional assembled view of the optical coupler 170 of FIG. 4 and additional components in accordance with embodiments of the split laser fiber 152.

In one embodiment, the optical coupler 170 comprises ferrules 186 and 188, and an adapter 190. The adapter 190 includes a central bore 192 that receives the end 194 of the ferrule 186 and the end 196 of the ferrule 188, as shown in FIG. 5. In one embodiment, the ends 194 and 196 have a frictional fit with the walls of the bore 192 to secure the ferrules 186 and 188 to the adapter 190. In one embodiment, nuts 198 secure the ferrules 186 and 188 to the adapter 190, as shown in FIG. 5. Other techniques may also be used to removably fasten the ferrules 186 and 188 to the adapter 190.

The ferrule 186 supports the distal end 168 of the extension laser fiber 163, and the ferrule 188 supports the proximal end 169 of the output laser fiber 164, as shown in FIG. 5. In one embodiment, the laser fibers 163 and 164 each include polymer cladding 200 surrounding a core 202, through which the electromagnetic energy is transmitted, in accordance with conventional optical fibers. In one embodiment, the cladding 200 of each of the laser fibers 163 and 164 is removed to expose the cores 202 at the distal end 168 and the proximal end 169 of the laser fibers 163 and 164, as shown in FIG. 5.

In one embodiment, each of the ferrules 186 and 188 includes a section 204 having a bore sized in accordance with the diameter of the cladding 200, as shown in FIG. 5. In one embodiment, the optical coupler 170 includes a disk 206 which is received within the ferrule 186 and/or 188 and has a central bore sized to receive and support the cladding 200 of the laser fibers 163 and 164.

In one embodiment, the ferrules 186 and 188 each include a section 208 having a bore that is sized to support the exposed cores 202, as shown in FIG. 5. In one embodiment, the core 202 of the extension laser fiber 163 has a polished flat surface at the terminating end that is substantially perpendicular to the longitudinal axis 210 of the fiber 163. In one embodiment, the exposed core 202 of the output laser fiber 164 has a polished flat surface that is substantially perpendicular to the longitudinal axis 212 of the output laser fiber 164. In one embodiment, the distal end 168 of the extension laser fiber 163 and the proximal end 169 of the output laser fiber 164 are supported by the optical coupler 170 such that the longitudinal axis 210 of the extension laser fiber 163 is substantially coaxial to the longitudinal axis 212 of the output laser fiber 164, as shown in FIG. 5.

In one embodiment, the flat terminating surfaces of the cores 202 of the extension laser fiber 163 and the output laser fiber 164 abut each other, or are positioned in close proximity to each other, to allow for the transmission of electromagnetic energy from the extension laser fiber 163 to couple to the output laser fiber 164. In one embodiment, a suitable optical coupler is used between the terminating ends of the laser fibers 163 and 164 to facilitate the delivery of electromagnetic energy discharged from the distal end 168 of the extension laser fiber 163 into the proximal end 169 of the output laser fiber 164.

In one embodiment, the adapter 190 is formed of metal, such as aluminum or other suitable metal. In one embodiment, the adapter 190 includes fins 214 that extend radially from the adapter 190. The fins 214 provide a large surface area to improve heat transfer from the adapter 190 to the surrounding environment.

Figure 6:
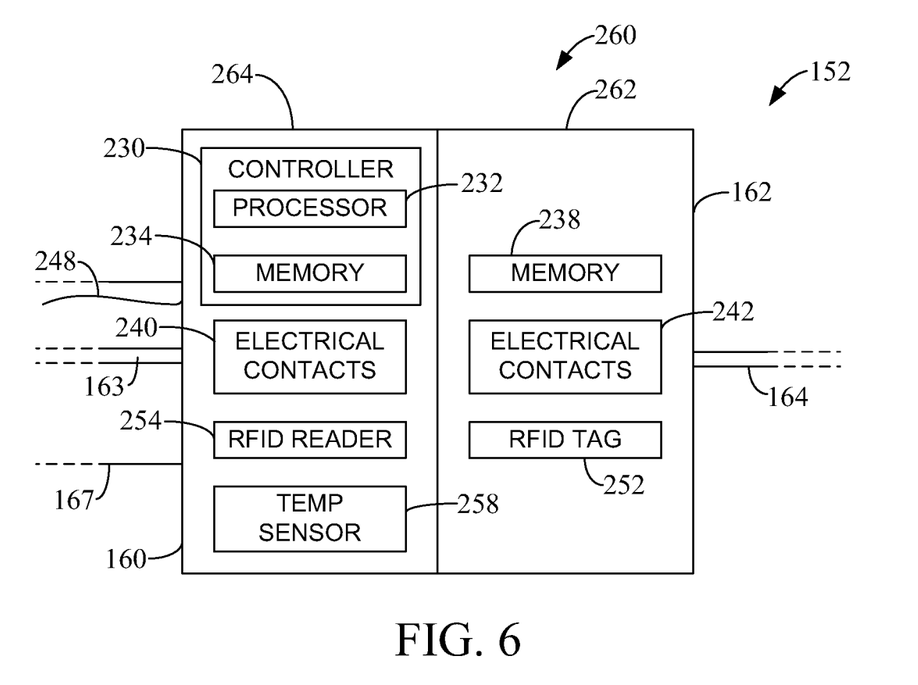
FIG. 6 is a schematic diagram of a junction between an extension member and an output member of a split laser fiber, in accordance with embodiments of the invention.

Additional embodiments of the laser system 150 include other features that are not found in conventional surgical laser systems. Reference will be made to FIG. 6, which is a schematic diagram of a junction between the extension member 160 and the output member 162 of a split laser fiber 152, in accordance with embodiments of the invention.

In one embodiment, the surgical laser tool 150 includes at least one controller, such as the controller 156 (FIG. 2). In one embodiment, the surgical laser tool 150 includes a controller 230 that is formed as a component of the extension member 160, as shown in FIG. 6. Embodiments of the tool 150 include the use of one or both of these controllers, each of which includes at least one processor 232 that is configured to execute program instructions stored in memory of the tool 150, or other location, to perform various functions in accordance with embodiments described herein. Further, it is understood that a controller located remotely from the tool 150 may also be used to perform various functions described herein. While the following discussion may reference the use of one of these controllers as performing a given function, it is understood that embodiments of the invention cover the performance of the function using any of these controllers.

In one embodiment, the surgical laser tool 150 is capable of retrieving or detecting output member information relating to the output member 162. Embodiments of the output member information include, for example, unique identification of the output member (e.g., a serial number or code), a type of the output member, an identification of a type of the probe tip (e.g., end-fire probe tip, side-fire probe tip, direction of laser discharge, etc.), a power rating for the output member, laser source settings, a laser wavelength range for the output member, an identification of a laser surgical treatment that the output member is configured to perform. The output member information can also include information relating to the laser surgical treatment performed using the output member 162. This may include, for example, a date of the laser surgical treatment, an identification of a physician who performed the treatment, the laser source settings for the treatment, a duration of the treatment, a count of the laser pulses delivered during the treatment, and other data relating to the treatment.

In one embodiment, the tool 150 stores extension member information relating to the extension member 160, which may be retrieved by the surgical laser tool. Exemplary extension member information includes a unique identification of the extension member (e.g., a serial number or code), a type of the extension member, a power rating for the extension member, laser source settings, a laser wavelength range for the extension member, an identification of a laser surgical treatment that the extension member is configured to perform. The extension member information can also include information relating to the laser surgical treatments performed using the extension member 162. This may include, for example, a date of the laser surgical treatment, an identification of a physician who performed the treatment, the laser source settings for the treatment, a duration of the treatment, a count of the laser pulses delivered during the treatment, and other data relating to the treatment.

The output member information and the extension member information may be stored in computer-readable memory that is accessible by the controller 230, the controller 156, or a remote controller using conventional data communication protocols. The memory may be local memory, such as memory 233 located outside the split fiber 152, memory 234 of the extension member 160, or memory 238 of the output member 162, as illustrated in FIGS. 2 and 6. Alternatively, the memory in which the output member information is stored may be remote from the surgical laser tool 150. The controller 230 and/or the controller 156 may access the remote memory using conventional data communication techniques, such as over a network.

In one embodiment, at least one controller (e.g., 230 or 156) of the tool 150 is configured to store and/or modify the output member information and the extension member information. As a result, the information may be updated to log usage of the components.

In one embodiment, at least one controller of the tool 150, such as the controller 156 or the controller 230, is configured to display the output member information and/or the extension member information on the display 239 of the tool 150. Alternatively, the output member information and/or the extension member information may be accessed through a suitable network connection to the memory or database in which the information is stored using a suitable computing device (e.g., computer, a mobile device, etc.) in accordance with conventional techniques.

In one embodiment, the output member information is accessed by the controller 230 and/or the controller 156 through an electrical connection between the extension member 160 and the output member 162. In one embodiment, the extension member 160 includes electrical contacts 240, one or more of which are configured to engage electrical contacts 242 of the output member 162 when they are properly joined together, as illustrated schematically in FIG. 6.

Figure 7:
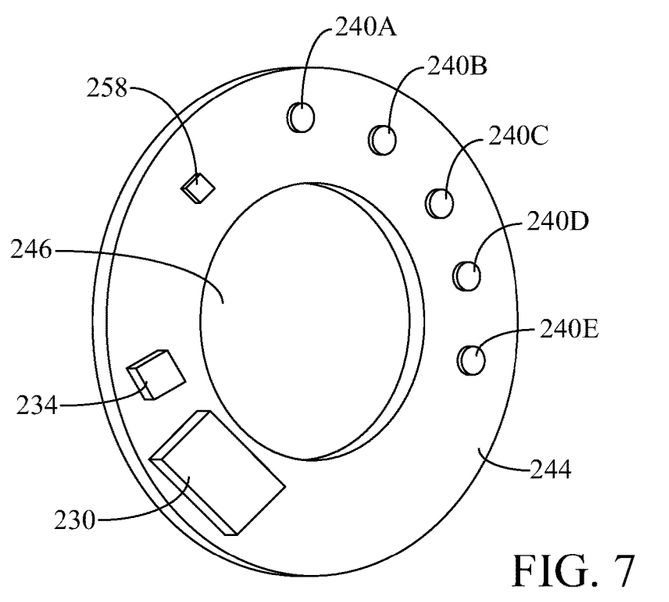
FIG. 7 is a simplified diagram of an electronics board in accordance with embodiments of the invention.

In one embodiment, the electrical contacts 240 are supported on an electronic board or circuit board 244, as shown in FIG. 7, which is a simplified isometric view of the electronics board 244 in accordance with embodiments of the invention. Alternatively, the electrical contacts 240 may be supported on another component of the extension member 160, such as a connector, as shown in FIG. 5. In one embodiment, the electronic board 244 or other component that supports the electrical contacts 240 includes an aperture 246, through which the portions of the optical coupler 170 and the extension laser fiber 163 may extend. The electrical contacts 240 may comprise one or more electrical contacts, such as electrical contacts 240A-E, as shown in FIG. 7.

As mentioned above, the electrical contacts 242 are positioned to engage one or more of the electrical contacts 240 of the output member 162. In one embodiment, the engagement between the electrical contacts 240 and the electrical contacts 242 allows the controller 230 and/or the controller 156 to access output member information relating to the output member 162.

In accordance with one embodiment, the engagement between the electrical contacts 240 and the electrical contacts 242 form a circuit having a configuration that provides electrical feedback that can be used to distinguish different types of output members 162 from each other. The different types of electrical feedback generated by the different output members 162 can be mapped in memory of the tool 150 to corresponding output member information. Thus, the electrical feedback detected by the controller 230 or 156 of the tool 150 through the engagement between the electrical contacts 240 and the electrical contacts 242 can be used to identify the type of output member 162 that is being used and/or other output member information. This identification information can be used by the controller 230 or 156 to look up additional output member information for the member 162 through a look-up table or other method to access additional output member information stored in memory of the tool 150. For instance, the electrical feedback received by the controller 230 or 156 may indicate that the output member is a specific type. The controller can then access other output member information stored in memory of the tool 150 or memory located remotely from the tool 150 using the identified type. This allows the system 150 to distinguish various types of output members 162 from each other, such as output members 162 having an end-fire probe tip 132 from output members 162 having a side-fire probe tip 132, for example.

The controller 230 may be attached to the extension member 160, such as on the electronics board 244, as shown in FIG. 7. The controller 230 may also be located external to the extension member 150 as another component of the system 150, such as controller 156, in which case one or more electrical wires 248 (FIGS. 5 and 6) may be used to connect the contacts 240 and other electrical components of extension member 160 or output member 162 to the controller 230.

Figure 8:
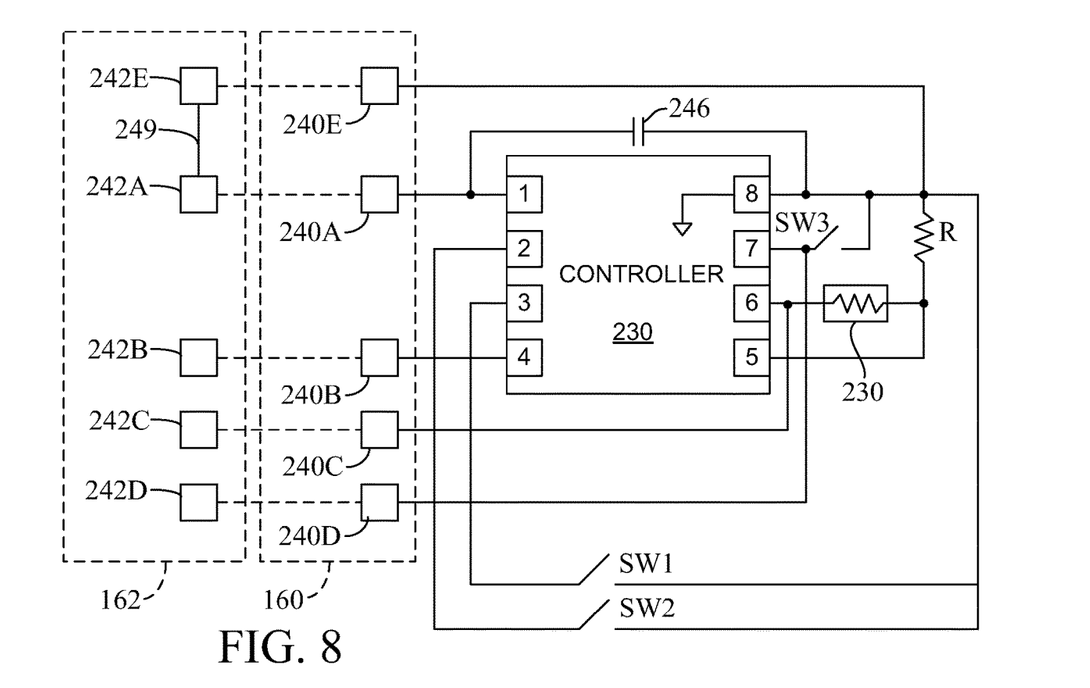
FIG. 8 is a schematic diagram of a circuit that may be used in connection with the electronics board of FIG. 7, in accordance with embodiments of the invention.

FIG. 8 is an exemplary schematic diagram of an electrical circuit that can be used to detect different circuit arrangements and electrical feedback produced through engagement of the electrical contacts 242 of the output member 162 and the electrical contacts 240 of the extension member 160. In one embodiment, the circuit is formed on the electronic board 244. Alternatively, a portion of the circuit may be supported by the extension member 160 while other portions are located external to the extension member 160.

In one embodiment, the controller 230 comprises an integrated circuit chip, such as the PIC12LF1822MF microchip produced by MCU, that includes a plurality of pins that may be connected in a suitable manner to detect the circuit configuration formed by the engagement of the contacts 240 and 242. For instance, pins 1 and 8 of the controller 230 may be coupled through a capacitor 246. Electrical contact 240E may be connected to the ground pin 8, electrical contact 240A may be connected to pin 1, electrical contact 240B may be connected to pin 4, electrical contact 240C may be connected to pin 6, and electrical contact 240D may be connected to pin 7, as illustrated in FIG. 8.

The mating of the extension member 160 to the output member 162 preferably aligns the contacts 242 with the contacts 240 in a desired manner. For example, the proper mating of the extension member 160 to the output member 162 may place the electrical contact 242A in engagement with electrical contact 240A, electrical contact 242B in engagement with electrical contact 240B, electrical contact 242C in engagement with electrical contact 240C, electrical contact 242D in engagement with electrical contact 240D, and electrical contact 242E in engagement with electrical contact 240E, as illustrated in FIG. 8. In the exemplary circuit of FIG. 8, electrical contact 242A is joined to the ground contact 242E through a suitable conductor 249. In other configurations, electrical conductors can be used to join the other available electrical contacts 242 to the electrical contact 240 corresponding to ground voltage to make other distinguishable circuit configurations.

In one embodiment, the circuit may include switches, such as SW1, SW2 and SW3, that are selectively activated through the engagement of the electrical contacts 242 with the electrical contacts 240. Other configurations for the circuit may also be used to provide the desired function of detecting multiple circuit configurations through the engagement of the electrical contacts 240 with the electrical contacts 242.

The controller 230 can use input voltages and other electrical feedback from the circuit formed through the coupling of the electrical contacts 240 of the extension member 160 to the electrical contacts 242 of the output member 162, such as that detected at the pins 1, 4, 6 and 7 in the exemplary circuit of FIG. 8, to determine the particular type of the output member 162 that is attached. In one embodiment, this electrical feedback is mapped to a certain type of output member 162 stored in memory of the system 150, such as memory 233, memory 234, memory 238, or other memory. This information can then be provided on the display 239 of the system 150 using, for example, the controller 156 (FIG. 2).

In accordance with another embodiment, the output member information for the output member 162 may be stored in memory 238 (FIG. 6) that is attached to the output member 162. In one embodiment, the memory 238 may be accessed by the controller 230 through the electrical contacts 240 and 242.

In accordance with another embodiment, the output member 162 may include a radio frequency identification (RFID) tag 252 (FIG. 6) that is attached to the output member 162 and contains the output member information or other identifier that may be used to access the output member information for the output member 162. In one embodiment, the extension member 160 includes an RFID tag reader 254 that is configured to communicate with the RFID tag 252 through the electrical contacts 240 and 242, or through a wireless communication link formed in accordance with conventional techniques. Information contained in the RFID tag 252 can then be accessed by the controller 230 or other processor of the system 150.

In one embodiment, the controller 230 and/or controller 156 uses the output member information to adjust the settings of the laser source 108. For instance, when the output member information indicates a power range, a laser energy wavelength or wavelength range, the controller 230 or controller 156 adjusts the settings of the laser source 108 accordingly. The laser source settings may also be adjusted based on a type of laser surgical procedure the output member 162 is configured to perform, or other information provided in the output member information. This safety feature can eliminate potential safety issues that may occur when the laser source settings are not set properly by the physician. In one embodiment, a controller of the tool 150 may adjust the settings of the laser source 108 based on the extension member information.

In one embodiment, the laser system 150 can detect when the output member 162 is not properly connected to the extension member 160 using the electrical contacts 240 and 242. In one embodiment, the controller 230 detects that the output member 162 is not properly connected to the extension member 160 when electrical signals or feedback received through the electrical contacts 240 indicate an error. This may involve not detecting voltage levels or other signals at one or more of the electrical contacts 242 that should be detected when the extension member 160 and the output member 162 are properly joined together. This may occur when the electrical contacts 242 do not properly engage the electrical contacts 240, or when the electrical contacts 242 do not engage the proper corresponding contact 240, for example. In one embodiment, upon detection of the connection error, the controller 230 and/or the controller 156 disables the ability of the system 150 to deliver laser pulses, and issues a warning to the operator, such as an audible warning and/or a visual warning provided on a suitable display 239 of the system 150, for example.

In one embodiment, the extension member 160 includes a temperature sensor 258, as shown in FIG. 6. In one embodiment, the temperature sensor 258 is configured to detect a temperature at the junction of the extension member 160 and the output member 162, such as at the optical coupler 170. In one embodiment, the temperature sensor 258 is configured to communicate temperature information to the controller 230 or to the controller 156 of the system 150 through a suitable electrical connection, such as one or more wires 248 (FIG. 6). In one embodiment, the output from the temperature sensor 258 is compared to a threshold level using one of the controllers of the tool 150. If the output from the temperature sensor 258 exceeds the threshold level, a warning is issued to the operator of the system 150, and/or the tool 150 is deactivated to prevent further delivery of laser energy pulses through the fiber 152. This threshold level may be a property of the output member 162 that is stored as output member information in memory of the tool 150 (e.g., memory 238, RFID tag 252, etc.) that is accessible by a controller of the tool 150 when the output member 162 is properly connected to the extension member 160.

In one embodiment, the temperature sensor 258 may be supported on the electronics board 244, as shown in FIG. 7. One exemplary temperature sensor 258 is a thermistor that may be used along with the resistor R to form a voltage divider, as illustrated in the exemplary circuit of FIG. 8. In one embodiment, the controller 230 provides a voltage to pin 6 and the voltage between the legs of the voltage divider is sampled at pin 5 using the controller 230. In one embodiment, this sampled voltage represents the temperature sensed by the sensor 258.

The extension member 160 has a limited lifespan. In one embodiment of the invention, the extension member information regarding the extension member 160 is logged in memory 233, memory 234 of the extension member 160, memory 238 of the output member 162, or memory located remotely from the tool 150, to assist in the determination of when the extension member 160 should be replaced. In one embodiment, the extension member information includes usage information, such as the date the extension member 160 was last used, a list of the output members 162 used with the extension member 160 and data relating to the treatments performed using the output members 162, a usage counter indicating either the aggregate use of the output member and/or a remaining usage amount that is available before the extension member 160 should be discarded. The use of the extension member 160 may be measured in terms of a duration that laser energy is delivered through the extension member 160, the number of laser pulses delivered through the extension member 162, the total power of laser energy delivered through the extension member 160, or other measurement. In one embodiment, the usage information is updated by the controller 230 or the controller 156 after each laser pulse is transmitted through the output member. In one embodiment, the controller 230 or the controller 156 prevents the use of the output member 160 with the tool 150 when the aggregate use for the extension member 160 reaches a predetermined threshold usage amount, or the remaining usage amount drops to zero. In one embodiment, the controller 156 or 230 issues a warning to the user of the tool 150, such as an audible warning, or a visual warning on the display 239 when the aggregate use of the extension member reaches a predetermined threshold amount.

In one embodiment, the split laser fiber 152 includes a connector 260 that secures the output member 162 to the extension member 160. In one embodiment, the connector 260 includes a connector member 262 attached to the output member 162 and a connector member 264 attached to the extension member 160, which are represented schematically in FIG. 6. Embodiments of the connector 260 are also shown in FIGS. 3 and 5. In one embodiment, the connector members 262 and 264 are generally configured to attach to each other using any suitable technique, such as a quick release mechanism comprising a latch releasable by a button 266 (FIG. 3) or other conventional coupling mechanism, that allows the connector member 262 and the attached output laser member 162 to be removably attached to the connector member 264 and the attached extension laser member 160 by hand.

In some embodiments, the connector member 264 supports the circuit or electronic board 244, the controller 230, memory 234, the electrical contacts 240, the RFID reader 254, and/or the temperature sensor 258, as illustrated in FIG. 6. In some embodiments, the connector member 262 supports the memory 238, the electrical contacts 242, and/or the RFID tag 252, as illustrated in FIG. 6. In one embodiment, the connector member 262 supports the electrical contacts 242 and the connector member 264 supports the electrical contacts 240, as shown in FIGS. 5 and 6.

In one embodiment, attachment of the connector member 262 to the connector member 264 causes the electrical contacts 242 to engage the electrical contacts 240. In one embodiment, grooves, slots or other guides are included on engaging surfaces of the connector members 264 and 266 to force the connector members 264 and 266 to be joined in a single orientation to each other. This ensures that the electrical contacts 242 engage the corresponding contacts 240 when the connector members 264 and 266 are secured together.

In one embodiment, the connector member 262 surrounds the ferrule 188 and the connector member 164 surrounds the ferrule 186, as shown in FIG. 5. In one embodiment, attachment of the connector member 262 to the connector member 264 secures the ferrules 186 and 188 in the adapter 190.

Figure 9:
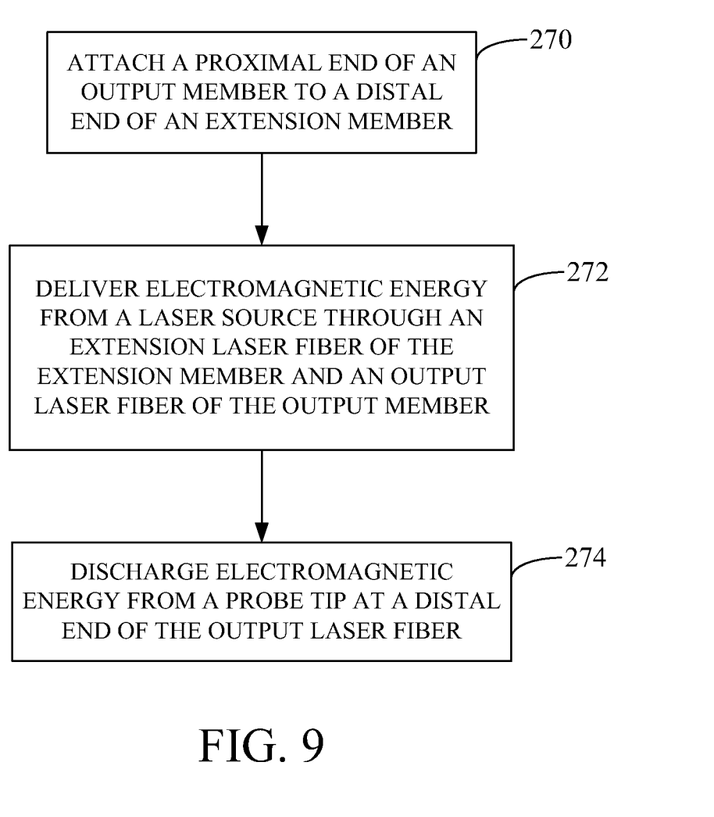
FIG. 9 is a flowchart illustrating a method in accordance with embodiments of the invention.

FIG. 9 is a flowchart illustrating a method in accordance with embodiments of the invention. At 270, a proximal end 169 of an output member 162 is attached to a distal end 168 of an extension member 160. At 272, electromagnetic energy 102 is delivered from a laser source 108 through an extension laser fiber 163 of the extension member 160 and an output laser fiber 164 of the output member 160. At 274, electromagnetic energy 102 is discharged from a probe tip 132 at a distal end 171 of the output laser fiber 164, as illustrated in FIG. 2. In one embodiment, a condition of a patient is treated responsive to step 274. Such treatments include, for example, tissue ablation treatments, kidney stone fragmentation, and other laser surgical treatments.

In one embodiment of the method, output information stored in memory (e.g., memory 233, memory 234, memory 238) of the tool 150 relating to the output member 162 is accessed using a processor, such as the processor 232 of the controller 230, a processor of the controller 156, or other processor. Exemplary embodiments of the output member information include a unique identification of the output member 162, a type of the output member 162, an identification of a type of the probe tip 132, a power rating for the output member 162, laser source settings for the output member 162, a laser wavelength range for the output member 162, and an identification of a laser surgical treatment that the output member 162 is configured to perform.

In one embodiment, the attaching step 270 comprises engaging electrical contacts 242 of the output member 162 with electrical contacts 240 of the extension member 160, such as discussed above with reference to FIGS. 5 and 6. In one embodiment, the output information is accessed using the engagement of the electrical contacts 242 with the electrical contacts 240. In one embodiment, electrical feedback from the electrical contacts 240 is received using a processor and the output member information is accessed based on the electrical feedback, as discussed above.

In accordance with another embodiment, the output member 162 includes memory 238, in which the output member information is stored. In one embodiment, the controller 230 or the controller 156 accesses the output member information stored in the memory 238 through the electrical contacts 240 and 242, as described above.

In accordance with another embodiment, the output member 162 includes an RFID tag 252 containing the output member information. In one embodiment, the extension member 160 includes an RFID reader 254 that is configured to access the output member information in the RFID tag 252.

In one embodiment, the controller 230 or the controller 156 is configured to determine whether the output member 162 is properly attached to the extension member 160 based on the electrical feedback received through the electrical contacts 240 and 242. In one embodiment, when it is determined that the output member 162 is not properly attached to the extension member 160 based on the electrical feedback, the tool 150 prevents the discharge of the electromagnetic energy 102. This ensures that the tool 150 is properly configured for the safe discharge of the electromagnetic energy 102.

In one embodiment, a processor of the controller 230 or 156 adjusts settings of the laser source 108 responsive to accessing the output member information. For instance, the controller 230 or 156 may adjust a power setting of the laser source 108, a wavelength of the electromagnetic energy 102 discharged by the laser source 108, a pulse frequency of the electromagnetic energy 102 discharged by the laser source 108, or other setting of the laser source 108 based on the output member information.

Although the present invention has been described with reference to preferred embodiments, workers skilled in the art will recognize that changes may be made in form and detail without departing from the spirit and scope of the invention.

What is claimed is:

1. A surgical laser tool comprising an output member, the output member comprising:
   an output laser fiber having a polished proximal end configured for attachment to a distal end of an extension laser fiber;
   a probe tip attached to a distal end of the output laser fiber for discharge of electromagnetic energy transmitted therethrough;
   a ring-shaped support, supported at a proximal end of the output member, the ring-shaped support including a central throughhole, wherein the central throughhole is coaxial with one or both of the extension laser fiber and the output laser fiber;
   a first electrical contact supported on the ring-shaped support; and
   an optical coupler configured to connect the distal end of the extension laser fiber to the proximal end of the output laser fiber, the optical coupler comprising:
   a first ferrule including a first ferrule end;
   a second ferrule including a second ferrule end; and
   an adapter including a central bore that receives the first ferrule end and the second ferrule end.

2. The tool of claim 1, wherein the output laser fiber and the probe tip are coaxially arranged along a central longitudinal axis of the output member; and
   wherein the output member is formed as a single attachment unit configured to couple to an extension member.

3. The tool of claim 2, further comprising:
   the extension member having a distal end removably coupleable to the proximal end of the output member, the extension member comprising the extension laser fiber.

4. The tool of claim 3, further comprising a second electrical contact supported at the distal end of the extension member, wherein the first electrical contact protrudes from a distalmost end of the ring-shaped support, and wherein the first and second electrical contacts are engageable when the extension member is coupled to the output member.

5. The tool of claim 4, further comprising a controller on the ring-shaped support configured to detect electrical feedback from the output member through the second electrical contact and determine whether the output member is properly coupled to the extension member based on the electrical feedback.

6. The tool of claim 5, wherein:
   the tool comprises a memory, the memory containing output member information including one or more of a unique identification of the output member, a type of the output member, an identification of a type of the probe tip, a power rating for the output member, laser source settings, a laser wavelength range for the output member, or an identification of a laser surgical treatment that the output member is configured to perform; and
   the controller accesses the output member information based on the electrical feedback.

7. The tool of claim 6, further comprising a temperature sensor configured to detect a temperature proximate the distal end of the extension member and the proximal end of the output member,
   wherein the output laser fiber includes an exposed core at the proximal end thereof, the polished proximal end of the output laser fiber being substantially perpendicular to a longitudinal axis of the output laser fiber,
   wherein the extension laser fiber includes an exposed core at the distal end, the exposed core having a polished flat surface at a terminating end that is substantially perpendicular to a longitudinal axis of the extension laser fiber,
   wherein the first ferrule supports the distal end of the extension laser fiber,
   wherein the second ferrule supports the distal end of the output laser fiber,
   wherein the adapter includes a plurality of fins, and
   wherein the optical coupler connects together a first connector member of the of the output member and a second connector member of the extension member, such that a radially exteriormost wall of the first connector member axially surrounds a portion of a radially exteriormost wall of the second connector member.

8. The tool of claim 5, wherein:
the tool comprises a laser source configured to deliver electromagnetic energy to a proximal end of the extension laser fiber; and
the controller is configured to adjust settings of the laser source based on the electrical feedback.

9. The tool of claim 5, wherein:
the tool comprises a memory supported at the proximal end of the output member; and
the controller is configured to log use of the extension member in the memory.

10. A surgical laser tool comprising an output member, the output member comprising:
an output laser fiber configured for attachment to a distal end of an extension laser fiber;
a probe tip attached to a distal end of the output laser fiber for discharge of electromagnetic energy transmitted therethrough;
a first optical coupler optically connecting a proximal end of the output laser fiber to the distal end of the extension laser fiber;
a ring-shaped support separate from the first optical coupler and coaxial with both of the extension laser fiber and the output laser fiber; and
an electrical contact supported on the ring-shaped support.

11. The tool of claim 10, further comprising:
a first connector member at a proximal end of the output member, the first connector member including a proximal surface and a protrusion extending proximally from the proximal surface, the protrusion encircling the first optical coupler and having a first interior surface configured to support the first optical coupler, and a second interior surface, proximal to the first interior surface and spaced radially outward of the first interior surface, configured to receive an extension member; and
a first electrical contact supported on a proximally facing surface of the protrusion;
wherein the output laser fiber, the probe tip, the first optical coupler, and the first connector member are coaxially arranged along a central longitudinal axis of the output member.

12. The tool of claim 11, wherein the tool further includes:
the extension member, wherein the extension member includes a distal end including a second connector member removably coupleable with the second interior surface of the first connector member, the extension member comprising an extension laser fiber;
a second optical coupler removably coupleable with the first optical coupler to optically connect the distal end of the extension laser fiber to the proximal end of the output laser fiber,
a second electrical contact supported on a distal surface of the second connector member, wherein the first and second electrical contacts are engageable when the first connector member is coupled to the second connector member; and
a controller configured to detect electrical feedback through the second electrical contact.

13. The tool of claim 12, further comprising:
a laser source that is configured to deliver electromagnetic energy to a proximal end of the extension laser fiber; and
the controller comprising a processor configured to adjust settings of the laser source based on the electrical feedback.

14. The tool of claim 10, wherein the first optical coupler connects together a first connector member of the output laser fiber and a second connector member of the extension laser fiber, such that a radially exteriormost wall of the first connector member axially surrounds a portion of a radially exteriormost wall of the second connector member.

15. A method comprising:
attaching a first connector member at a proximal end of an output member to a second connector member at a distal end of an extension member, wherein an optical coupler connects together the first connector member and the second connector member, such that: a surface of the first connector member is coupled with a surface of the second connector member, a first electrical contact supported on the first connector member is engaged with a second electrical contact supported on the second connector member such that a radially exteriormost wall of the first connector member axially surrounds a portion of a radially exteriormost wall of the second connector member;
delivering electromagnetic energy from a laser source through an extension laser fiber of the extension member and an output laser fiber of the output member; and
discharging electromagnetic energy from a probe tip attached to a distal end of the output laser fiber.

16. The method of claim 15, wherein a memory is supported on the first connector member, the method further comprising accessing an output information stored in the memory relating to the output member using a processor, the output member information including one or more of a unique identification of the output member, a type of the output member, an identification of a type of the probe tip, a power rating for the output member, laser source settings, a laser wavelength range for the output member, or an identification of a laser surgical treatment that the output member is configured to perform.

17. The method of claim 16, further comprising adjusting settings of the laser source responsive to accessing the output member information using the processor.

18. The method of claim 15, further comprising:
receiving electrical feedback through the second electrical contact; and
adjusting settings of the laser source based on the electrical feedback.

19. The method of claim 15, further comprising:
receiving electrical feedback from the second electrical contact using a processor; and
determining whether the output member is coupled to the extension member based on the electrical feedback using the processor.

20. The method of claim 15, wherein the output laser fiber in the output member is coaxially aligned with and optically coupled to the extension laser fiber in the extension member, and the output member is formed as a single attachment unit configured to couple to the extension member.

* * * * *